United States Patent
Kirst et al.

(10) Patent No.: US 9,134,165 B2
(45) Date of Patent: Sep. 15, 2015

(54) METHOD FOR DETECTING ACCRETION OR ABRASION IN A FLOW MEASURING DEVICE

(75) Inventors: Michael Kirst, Lorrach (DE); Alfred Rieder, Landshut (DE); Wolfgang Drahm, Erding (DE); Hao Zhu, Freising (DE); Christof Huber, Bern (CH); Vivek Kumar, Allschwil (CH)

(73) Assignee: Endress + Hauser Flowtec AG, Reinach (CH)

( * ) Notice: Subject to any disclaimer, the term of this patent is extended or adjusted under 35 U.S.C. 154(b) by 430 days.

(21) Appl. No.: 13/565,158

(22) Filed: Aug. 2, 2012

(65) Prior Publication Data
US 2013/0031973 A1 Feb. 7, 2013

Related U.S. Application Data

(60) Provisional application No. 61/521,025, filed on Aug. 8, 2011.

(30) Foreign Application Priority Data

Aug. 4, 2011 (DE) ..................... 10 2011 080 415 U

(51) Int. Cl.
*G01K 13/12* (2006.01)
*G01F 25/00* (2006.01)
(Continued)

(52) U.S. Cl.
CPC .......... *G01F 25/0007* (2013.01); *G01B 21/085* (2013.01); *G01F 1/8436* (2013.01); *G01F 1/8477* (2013.01); *G01N 3/56* (2013.01);
(Continued)

(58) Field of Classification Search
USPC ..................... 374/102; 73/204, 861; 378/147; 376/409
See application file for complete search history.

(56) References Cited

U.S. PATENT DOCUMENTS 3,913,378 A * 10/1975 Hausler .............................. 374/7
5,152,049 A * 10/1992 McQueen ...................... 29/611
(Continued)

FOREIGN PATENT DOCUMENTS

DE    102009000067 A1    8/2010
EP        0977008 A2       2/2000
(Continued)

OTHER PUBLICATIONS

Holdsworth et. al. ("Thermal processing of packaged foods" (2007) Springer ISBN: 978-0-387-72249-8).*

(Continued)

*Primary Examiner* — Andre Allen
(74) *Attorney, Agent, or Firm* — Bacon & Thomas, PLLC

(57) ABSTRACT

A method for detecting accretion or abrasion on a first measuring tube of a flow measuring device. A first temperature as a function of time is registered via a first temperature sensor, which is arranged on the first measuring tube in such a manner that, between the first temperature sensor and the medium, at least one measuring tube wall of the first measuring tube is embodied. Parallel in time, a second reference temperature as a function of time is registered by a second temperature sensor, which is spaced from the first temperature sensor and thermally coupled to the medium. Therefrom, at least one variable characteristic is determined, and accretion or abrasion on the first measuring tube is detected, if the at least one determined characteristic variable or a variable derived therefrom deviates by more than a limit value from a predetermined reference variable.

13 Claims, 3 Drawing Sheets

(51) Int. Cl.
*G01B 21/08* (2006.01)
*G01N 3/56* (2006.01)
*G01N 17/00* (2006.01)
*G01F 1/84* (2006.01)
*G01K 3/04* (2006.01)
*G01B 11/06* (2006.01)

(52) U.S. Cl.
CPC .............. *G01N17/008* (2013.01); *G01B 11/06* (2013.01); *G01K 3/04* (2013.01)

(56) References Cited

U.S. PATENT DOCUMENTS

| | | | | | |
|---|---|---|---|---|---|
| 5,248,198 | A | * | 9/1993 | Droege | 374/7 |
| 5,353,653 | A | * | 10/1994 | Watanabe et al. | 73/865.9 |
| 6,367,306 | B1 | * | 4/2002 | Kitano | 73/1.27 |
| 6,386,272 | B1 | * | 5/2002 | Starner et al. | 165/11.1 |
| 6,886,393 | B1 | * | 5/2005 | Romanet et al. | 73/61.62 |
| 8,302,491 | B2 | * | 11/2012 | Stack | 73/861.356 |
| 2011/0029259 | A1 | * | 2/2011 | Cunningham et al. | 702/47 |
| 2011/0308548 | A1 | * | 12/2011 | Amundsen et al. | 134/18 |

FOREIGN PATENT DOCUMENTS

| | | |
|---|---|---|
| FR | 2266869 | 10/1975 |
| FR | 2754898 A1 | 4/1998 |
| WO | 2009051588 A1 | 4/2009 |
| WO | 2009134268 A1 | 11/2009 |
| WO | 2010087724 A1 | 8/2010 |

OTHER PUBLICATIONS

German Srch Rpt, Jun. 5, 2012, Munich.
Intl Srch Rpt, Oct. 31, 2012, The Netherlands.
English translation of IPR, WIPO, Geneva, Feb. 13, 2014.

* cited by examiner

METHOD FOR DETECTING ACCRETION OR ABRASION IN A FLOW MEASURING DEVICE

CROSS-REFERENCE TO RELATED APPLICATION

This application is a Nonprovisional Application which claims the benefit of U.S. Provisional Application No. 61/521,025, filed on Aug. 8, 2011, and also claims the benefit of German application 10 2011 080 451.3 filed on Aug. 4, 2011.

TECHNICAL FIELD

The present invention relates to a method for detecting accretion or abrasion on a first measuring tube of a flow measuring device flowed through by medium, as well as to a correspondingly embodied flow measuring device.

BACKGROUND DISCUSSION

Flow measuring devices, such as, for example, vortex flow measuring devices and Coriolis flow measuring devices, include, as a rule, at least one measuring tube. Coriolis flow measuring devices can, in such case, also have two or more (for example, four) measuring tubes embodied so as to be fluidically parallel to one another. Depending on application, there is a problem, in such case, when accretion forms on the measuring tubes of the flow measuring devices (especially due to at least one part of the medium to be measured), or when abrasion (e.g. due to a corrosion) occurs on the surfaces of the respective measuring tubes contacting the medium. Especially in the case of Coriolis flow measuring devices, the oscillatory behavior of the relevant measuring tube is influenced by such accretion formation or abrasion, which in turn can lead to measurement errors in the case of measurement of a physical, measured variable (e.g. mass flow, density, viscosity, etc.). Furthermore, accretion formation as well as corrosion on measuring tubes is also problematic when a contamination of the respective medium to be measured, e.g. due to detachment of parts of the deposit, should be prevented. This is, for example, the case in food industry applications. Accordingly, it is desirable that such accretion formation and/or abrasion of a measuring tube of a flow measuring device be detectable in a reliable and simple manner, without removal of the flow measuring device or some other substantial intervention being required. In this connection, the detection of a layer-like accretion on the inner wall of a measuring tube is especially difficult to detect, since fluid can, in such case, still flow through the measuring tube in question.

In the publication WO 20091134268 A1, a flow measuring device is described, via which a deviation in a flow measuring device parameter is detectable. Such a parameter deviation can be bought about by, among other things, a plugging of a measuring tube and/or by accretion forming on a measuring tube. In the case of a described method, temperature measurements are performed at different positions of the flow measuring device, such as, for example, on the inlet side and outlet side, or alternatively, on a first measuring tube and on a second measuring tube. Therefrom, a temperature gradient is ascertained. A deviation in a flow measuring device parameter is then detected, when the ascertained temperature gradient exceeds a limit value. The method is based on the assumption that by accretion formation or plugging influences the flow through the relevant measuring tube, which, in turn, affects the temperature gradients.

SUMMARY OF THE INVENTION

Accordingly, an object of the present invention is to provide a method and a flow measuring device, via which accretion formation and/or abrasion on a measuring tube of the flow measuring device is detectable early and in a reliable manner.

The object is achieved by the features of a method as well as by a flow measuring device.

In the present invention, a method is provided for detecting accretion or abrasion on a first measuring tube of a flow measuring device flowed through by medium. In such case, the method comprises steps as follows:

A) registering a first temperature as a function of time via a first temperature sensor, which is arranged on the first measuring tube in such a manner that, between the first temperature sensor and the medium, at least one measuring tube wall of the first measuring tube is present; and, parallel in time, registering a second reference temperature as a function of time via a second temperature sensor, which is spaced from the first temperature sensor, and is thermally coupled to the medium;

B) determining, from at least the first temperature as a function of time and the second reference temperature as a function of time, at least one variable characteristic for heat transfer from the medium through the measuring tube wall to the first temperature sensor; and C) detecting accretion or abrasion on the first measuring tube, if the at least one determined characteristic variable or a variable derived therefrom deviates by more than a limit value from a predetermined reference variable.

In the present invention, the principle is utilized that, due to accretion formation on the first measuring tube or due to abrasion on the first measuring tube, heat transfer properties from the medium through the measuring tube wall of the first measuring tube (and, in given cases, through other components arranged between the medium and the first temperature sensor) to the first temperature sensor are changed. Such changed heat transfer properties lead, in turn, especially in the case of occurrence of a temperature change of the medium, to a changed temperature adjustment in the region of the first measuring tube (or the first temperature sensor). A change in heat transfer properties from the medium through the measuring tube wall of the first measuring tube to the first temperature sensor can especially be determined by the temperature adjustment in the region of the first measuring tube in the case of occurrence of a temperature change of the medium being registered via sensor, and being compared with a temperature adjustment at another position of the flow measuring device, which is spaced from the first, which is likewise thermally coupled to the medium, and which serves as reference. According to the present invention, this occurs by registering the first temperature as a function of time, and the second temperature as a function of time as reference. Since the second temperature sensor is arranged spaced from the first temperature sensor and is thermally coupled to the medium, in the case of occurrence of a temperature change of the medium, the temperature adjustment of the second temperature sensor is completely or largely (depending on position of the second temperature sensor) independent of a possibly occurring accretion formation or abrasion on the first measuring tube. In line with this, according to the present invention, a change in given cases occurring in heat transfer properties from the medium through the measuring tube wall of the first measuring tube to the first temperature sensor as compared to an original starting state of the flow measuring device can be detected reliably and in simple manner, and therewith accretion formation and/or abrasion on the first measuring tube. The method is implementable in a relatively cost effective manner, since in the case of flow measuring devices, as a rule, temperature sensors are provided anyway, especially for performing temperature compensation in the determining the physical, measured variable of the medium sought to be measured. Furthermore, the method of the invention can also be performed in parallel with a flow measurement (e.g. for determining mass flow, density and/or viscosity of the medium), and/or even in the case of medium at rest.

The present invention is especially advantageous, because a layer-like accretion (and correspondingly also abrasion) on the inner wall of a measuring tube is detectable, even when, through the measuring tube in question, an unreduced or only slightly reduced (or, in the case abrasion, a slightly increased) flow cross section is provided. Via the present invention, also other forms of accretion are, however, detectable. It is especially also detectable whether the measuring tube in question is completely plugged, since due to the plugging, heat transfer from the medium through the plugged part of the medium and through the measuring tube wall to the first temperature sensor likewise significantly deviates from heat transfer in a starting state of the flow measuring device.

Referred to as a "flow measuring device" in the present relationship is generally any device, via which at least one physical, measured variable (especially a mass flow, density and/or viscosity) of a medium flowing in a pipeline is detectable. Such a flow measuring device can be formed, for example, by a vortex flow measuring device or by a Coriolis flow measuring device. The flow measuring device can, in such case, have one measuring tube, or alternatively also two or more measuring tubes, if it has a number of measuring tubes, these are then especially connected so as to be fluidically parallel to one another. The flow measuring device especially includes a measuring transducer of vibration type, which in turn has at least the first measuring tube, and, in given cases, also a second or a number of other measuring tubes. A measuring transducer of vibration type serves, in such case, generally to produce mechanical reaction forces in a flowing medium, e.g. mass flow dependent, Coriolis forces, density dependent, inertial forces and/or viscosity dependent, frictional forces. These mechanical reaction forces are, in turn, registerable by sensor. A typical manner of operation of such a flow measuring device will now be described: All measuring tubes of the measuring transducer are excited by at least one exciter to execute mechanical oscillations. In such case, especially the fundamental bending oscillation mode can be excited. Furthermore, the mechanical oscillations of the measuring tube, or tubes, are registered by at least one, as a rule, at least two, oscillation sensors spaced along the direction of elongation of the measuring tube, or tubes. The sensor signals provided by the at least one oscillation sensor are evaluated by an electronics of the flow measuring device. The driving of the exciter occurs, as a rule, likewise via the electronics.

The flow measuring device is especially embodied as a Coriolis flow measuring device. With a Coriolis flow measuring device, the mass flow of the medium through the Coriolis flow measuring device is determinable making use of the Coriolis principle. If the measuring tubes are not flowed through by medium, in the case of excitation to mechanical oscillations, they then oscillate (along their respective directions of elongation) in phase. If the measuring tubes are flowed through by a medium (with a flow velocity greater than zero), this then leads to the measuring tubes being additionally deformed due to the Coriolis force acting on the flowing medium. This phase shift occurring from this along the lengths of the measuring tubes can be registered by the at least one oscillation sensor. For example, at least two oscillation sensors arranged spaced from one another along the direction of elongation of the measuring tubes can be provided. The phase shift is proportional to the mass flow rate.

Additionally or alternatively, also a density and/or a viscosity of the flowing medium can be determined by a flow measuring device incorporating a measuring transducer of vibration type. For determining the density of the medium, the principle utilized is that the resonance frequency (for example, of the fundamental mode of the bending oscillation) depends on the oscillating mass and therewith on the density of the flowing medium. Regardless of which physical, measured variable (mass flow, density, viscosity, etc.) is momentarily actually determined, or, in general, is determinable, by a flow device, such flow measuring devices with a measuring transducer of vibration type are frequently (and also in the present connection) generally referred to as Coriolis flow measuring devices. In a further development, the flow measuring device is formed by such a Coriolis flow measuring device. Through this, especially a mass flow, density and/or viscosity of the respective medium is/are determinable. Since such Coriolis flow measuring devices frequently have two or more measuring tubes in each case with narrowed flow cross sections (relative to the supplying and draining sections of a pipeline) and/or at least one curved measuring tube, the measuring tubes are especially endangered with respect to accretion and abrasion. As is explained above, accretion and abrasion on the measuring tubes is, however, especially critical, so that the method of the invention is especially advantageous especially in the case of Coriolis flow measuring devices.

The "medium" can be formed completely or also only partially by a liquid, a gas or a mixture of liquid and gas. The liquid, the gas or the mixture of liquid and gas can especially also entrain solid particles (for example, pneumatically conveyed dust, solid particles in gas, solid particles in liquid, etc.). It is not absolutely necessary that the medium flow during the detection method of the invention. Rather, it can be at rest. Furthermore, a medium change can even take place.

The steps of registering (step A)), determining (step B)) and detecting (step C)) are especially performed in the case of (especially directly during or after) occurrence of a (continuous or abrupt) temperature change in the medium. According to a further development, the temperature change is not induced by the flow measuring device. Such a temperature change not induced by the flow measuring device is, for example, present when the temperature of the relevant medium changes or when a medium change takes place. A well suited occasion for performing the detection method of the invention is, for example, when a cleaning of the respective pipeline (and therewith also of the tubes of the flow measuring device) is performed, in which case the pipeline is rinsed with a cleaning medium (as a rule, hot steam). Such a cleaning is referred to especially as CIP (Cleaning In Process), Furthermore, depending on the application of the flow measuring device, process related temperature changes of the medium can occur, which in given cases also occur at predetermined times and/or at a predetermined level. In general, and especially when the temperature change is not induced by the flow measuring device, it is preferable that, via a temperature sensor, which is contacted by the medium or which is thermally coupled as directly as possible to the medium (e.g. via one or more components), the occurrence of such a temperature change—and, in given cases, also its size—is registerable. This temperature sensor can be formed by the above mentioned second temperature sensor or also by an additional temperature sensor (in addition to the first and the second temperature sensors). Especially after detection of such a temperature change, the detection method of the invention is started (for example, via an electronics of the flow measuring device).

The first temperature sensor can be arranged, for example, on the exterior of the first measuring tube, wherein it can either be provided directly on the first measuring tube or thermally coupled to the first measuring tube through a further, interposed component. The first temperature sensor can also extend partially into the measuring tube wall of the first measuring tube (e.g. be inserted into a corresponding blind bore), so that the measuring tube wall in this region is embodied so as to be somewhat thinner than in the surrounding regions.

In general, it should be noted that the opportunity also fundamentally exists to register additionally (via corresponding temperature sensors) temperatures at other positions, wherein these temperatures are likewise evaluated during the step of determining (step B)). Furthermore, in the case of the step of determining (step B)), still other influencing factors can also be taken into consideration. If the flow measuring device has a plurality of measuring tubes, the method of the invention is in a corresponding manner performed in parallel on a plurality of measuring tubes. If, in the case of the step of determining (step B)), a number of variables characteristic for heat transfer are determined, it can be provided that already in the case of deviation of a (single) variable by more than an (associated) limit value from a predetermined (associated) reference variable, accretion or abrasion has then been detected. Alternatively, however, it can also be provided that accretion or abrasion is detected only when two or more variables deviate by (respective, associated) limit values from (respective, associated) reference variables, and/or when a derived variable obtained from a mathematical combining of the respective variables characteristic for heat transfer deviates by more than a limit value from a predetermined reference variable.

In a further development, the method of the invention and also the additional steps of the subsequently explained further developments and variants are in each case performed internally in the flow measuring device. Especially, an electronics of the flow measuring device is embodied for performance of the respective steps. In connection with the present invention, it should in part be mentioned that "at least one" component is provided. In the case of these components, also in the case of the additional explanations, reference is made to the possibility for provision of a plurality of components (besides the possibility of exactly one component), even when this is not explicitly mentioned each time.

In a further development, the second temperature sensor is arranged so as to be in direct contact with the medium. In this way, a temperature change occurring in the medium can be registered directly, so that an influencing of this temperature registration by other influencing factors is eliminated as far as such is possible. The thermal coupling of the second temperature sensor to the medium especially remains invariant in time. Especially, the second temperature sensor protrudes into the flow path of the medium.

In a further development, between the second temperature sensor and the medium, at least a second component contacted by the medium is provided. Via the second component thus there occurs a thermal coupling of the second temperature sensor to the medium. Fundamentally, even a plurality of components can be provided between the second temperature sensor and the medium. In order to achieve an indirect temperature registration of the medium (indirect via the second component and, in given cases, via other components), an indirect temperature registration, which is as uninfluenced by additional influencing factors as possible, also in the case of this further development, it is preferable that the second temperature sensor is thermally coupled as directly as possible (i.e. exclusively via the second component, or, alternatively, via as few components as possible) to the medium. The second component forms, especially, a component of the flow measuring device, and is especially embodied separately from the first measuring tube. Since the second component is embodied separately from the first measuring tube, it is assumed that accretion or abrasion does not occur on the second component or does not occur to the same degree (with respect to its heat transfer properties from the medium to the second temperature sensor) as on the first measuring tube. In a further development, the second component is formed by a component of the flow measuring device embodied upstream from the first measuring tube. In this way, the occurrence of a temperature change of the medium is detectable early by the second temperature sensor.

In a further development, the second component is essentially invariant (or constant) as regards accretion and abrasion by the medium. In this way, in the region of the second temperature sensor, a reference is provided, which is constant or at least largely constant as regards heat transfer properties from the medium to the second temperature sensor. The thermal coupling of the second temperature sensor to the medium is especially invariant or at least largely invariant. This is especially advantageous for reliable detection of accretion or abrasion on the first measuring tube. By "essentially invariant" is meant, in such case, that accretion and/or abrasion either does not take place at all, or only takes place to a markedly lesser extent than in the case of the first measuring tube. For example, the second component can be formed by an inlet side flow divider, which is significantly less endangered with respect to accretion and/or abrasion than the (as a rule, two or more) measuring tubes.

The provision of a reference at least largely remaining the same as regards the reliability of accretion and/or abrasion detection on the first measuring tube is indeed preferable. Fundamentally, however, the above explained advantages can at least essentially also be achieved when the second component is not invariant with respect to accretion or abrasion, to the extent that accretion or abrasion does not occur on the second component to the same extent (with respect to heat transfer properties to the second temperature sensor) as in the case of the first measuring tube. In a further development, the second component is formed by a second measuring tube of the flow measuring device, wherein the second measuring tube is connected so as to be fluidically in parallel with the first measuring tube. In this way, temperatures as a function of time, registered at the first and second measuring tubes, can be compared with one another according to the method of the invention.

In a further development, the flow measuring device is formed by a Coriolis flow measuring device. The method especially includes the following additional step, which is performed, for example, in the context of registering a physical, measured variable of the medium:

D) exciting the first measuring tube to execute mechanical oscillations.

If the flow measuring device has two or more measuring tubes, especially all measuring tubes are excited to execute mechanical oscillations.

In a further development, the method further includes the following additional step:

E) changing a temperature of the medium.

In a further development, the change in the temperature of the medium is especially actively induced via the flow measuring device. This occurs especially by heating the medium in a section of the flow measuring device arranged upstream from the first and second temperature sensors, or by cooling the medium in a section of the flow measuring device arranged upstream from the first and second temperature sensors. In this way, a targeted temperature change for performing the detection method is producible. The heating occurs especially via at least one heating element. The cooling occurs especially via at least one cooling element. In such case, the heating element and/or the cooling element preferably protrudes into the flow path of the medium, so that a targeted and defined heat transfer to or from the medium is implementable. Alternatively, it is, however, fundamentally also an option to have the heating or cooling of the medium occur only indirectly, especially via one or more components (e.g. a measuring tube, a pipe connection piece, etc.). The heating element and/or the cooling element is/are arranged especially upstream from a branching of the flow path into two or more measuring tubes present in given cases. In a further development, the performing of a heating cycle and/or of a cooling cycle is controlled by an electronics of the flow measuring device. In parallel therewith or (directly) thereafter, the performing of at least the steps of registering (step A)), determining (step B)) and detecting (step C)) can be controlled via the electronics.

In a further development, the at least one variable characteristic for heat transfer is determined from the derivative with respect to time (i.e. d/dt) of the first temperature as a function of time and (the derivative with respect to time) of the second reference temperature as a function of time. In an additional further development, the at least one variable characteristic for heat transfer is determined from the derivative with respect to time (i.e. d/dt) of a curve obtained via a predetermined, mathematical combining of the first temperature as a function of time and of the second reference temperature as a function of time. By taking the derivative with respect to time, the temperature adjustment can be evaluated. Already after measurement of relatively short time intervals, from the respective temperature curve, its slope can be evaluated, and conclusions concerning the temperature adjustment can, in turn, be drawn therefrom. Especially, the respective curve obtained from the derivative with respect to time is in each case evaluated. For example, accretion or abrasion can in each case be detected when the curve obtained from the derivative with respect to time deviates by more than a limit value from a reference curve. Alternatively, it is, however, also possible that, first of all, the first temperature as a function of time as well as the second reference temperature as a function of time and/or the curve obtained from their mathematical combining is approximated by a corresponding approximation function, as is subsequently explained with reference to a further development, and then the derivative with respect to time of this approximation function or these approximation functions is taken and evaluated. Furthermore, besides the above explained further developments and variants, mathematically equivalent operations are also possible.

In a further development, in the case of the step of determining (step B)), the first temperature as a function of time and the second reference temperature as a function of time are combined with one another according to a predetermined, mathematical operation, the curve obtained therefrom is approximated with a predetermined, mathematical approximation function via conforming corresponding parameters of the approximation function, and the at least one variable characteristic for heat transfer is formed via at least one parameter value of the ascertained approximation function. Via the at least one parameter value, the curve of the approximation function—and therewith also the curve, which is obtained due to the mathematical combining—is characterized, or at least partially determined. Accordingly, the at least one parameter value is a variable characteristic for heat transfer from the medium through the measuring tube wall to the first temperature sensor. The predetermined, mathematical combining is generally formed by a mathematical operation, which is applied to the first temperature as a function of time and to the second reference temperature as a function of time. In such case, different mathematical combinings are fundamentally possible. In a further development, the predetermined, mathematical combining is a mathematical operation in the formed of a division of the first temperature as a function of time by the second reference temperature as a function of time. As an alternative variant, a taking of the difference between the first temperature as a function of time and the second reference temperature as a function of time, for example, is possible. By a "predetermined, mathematical approximation function" is meant a function with a predetermined construction or predetermined form, wherein its parameter values are to be adapted in the context of the approximation. Furthermore, besides the above explained further developments and variants, equivalent mathematical operations are also possible. Especially, the first temperature as a function of time and the second reference temperature as a function of time can also especially in each case first be approximated by an approximation function, and a mathematical combining of the two obtained approximation functions or also of individual parameters or of all parameters of such can then occur.

In a further development, the predetermined, mathematical approximation function is formed by the function $$ae^{-\frac{t}{\tau}},$$

wherein a and τ are parameters and t is time. In such case, the parameter a is also referred to as the amplification factor and the parameter τ is also referred to as the time constant. The function can, however, also have still other parameters, such as is the case, for example, in the following function:

$$ae^{-\frac{t}{\tau}+c} + d.$$

In a further development, the at least one determined variable characteristic for heat transfer is formed by the parameter value of the time constant of the approximation function. The time constant is, in such case, generally the at least one parameter of the approximation function, which describes the time change of the approximation function. The time constant can especially be determined from the derivative of the approximation function with respect to time. If the predetermined, mathematical combining is a mathematical operation in the form of a division of the first temperature as a function of time by the second reference temperature as a function of time and the curve obtained thereby is approximated by an approximation function of the form $$ae^{-\frac{t}{\tau}},$$

the time constant τ is then especially a measure for the temperature adjustment in the region of the first measuring tube relative to the reference. Accordingly, accretion or abrasion on the first measuring tube can reliably be detected in this way. The variable characteristic for heat transfer can, however, generally also be formed by the time constant of an approximation function of a differing form.

The present invention relates furthermore to a flow measuring device, via which at least one physical, measured variable, especially mass flow, density and/or viscosity, of a medium flowing in a pipeline is determinable. The flow measuring device includes, in such case, at least a first measuring tube, through which a flow path for at least one part of the respective medium (flowing in the pipeline) extends. Furthermore, it includes: at least a first temperature sensor, which is arranged on the first measuring tube in such a manner that, between the first temperature sensor and a flow path extending within the first measuring tube, at least one measuring tube wall of the first measuring tube is present; at least a second temperature sensor, which is spaced from the first temperature sensor and is thermally coupled to a section of the flow path extending within the flow measuring device; and an electronics. In such case, during use of the flow measuring device (especially in the case of occurrence of a temperature change of the respective medium), via the electronics, from at least a first temperature registered as a function of time by the first temperature sensor and a second reference temperature as a function of time registered parallel in time by the second temperature sensor, at least one variable, which is characteristic for heat transfer from the respective medium through the measuring tube wall to the first temperature sensor, is determinable. Furthermore, via the electronics, accretion or abrasion on the first measuring tube is detectable, if the at least one determined, characteristic variable or a variable derived therefrom deviates by more than a limit value from a predetermined reference variable.

Via the flow measuring device of the invention, essentially the advantages explained above with reference to the method of the invention are achieved. Furthermore, the same further developments and variants, which were explained above with reference to the method of the invention, are implementable in a corresponding manner. The above explained steps are especially executed via a correspondingly embodied electronics of the flow measuring device, insofar as this is technically sensible. The electronics of the flow measuring device can work in an analog and/or digital manner.

BRIEF DESCRIPTION OF THE DRAWINGS

The invention and other advantages and utilities thereof will now be explained in greater detail on the basis of the appended drawing, the figures of which show as follows.

DETAILED DESCRIPTION IN CONJUNCTION WITH THE DRAWINGS

Figure 1:
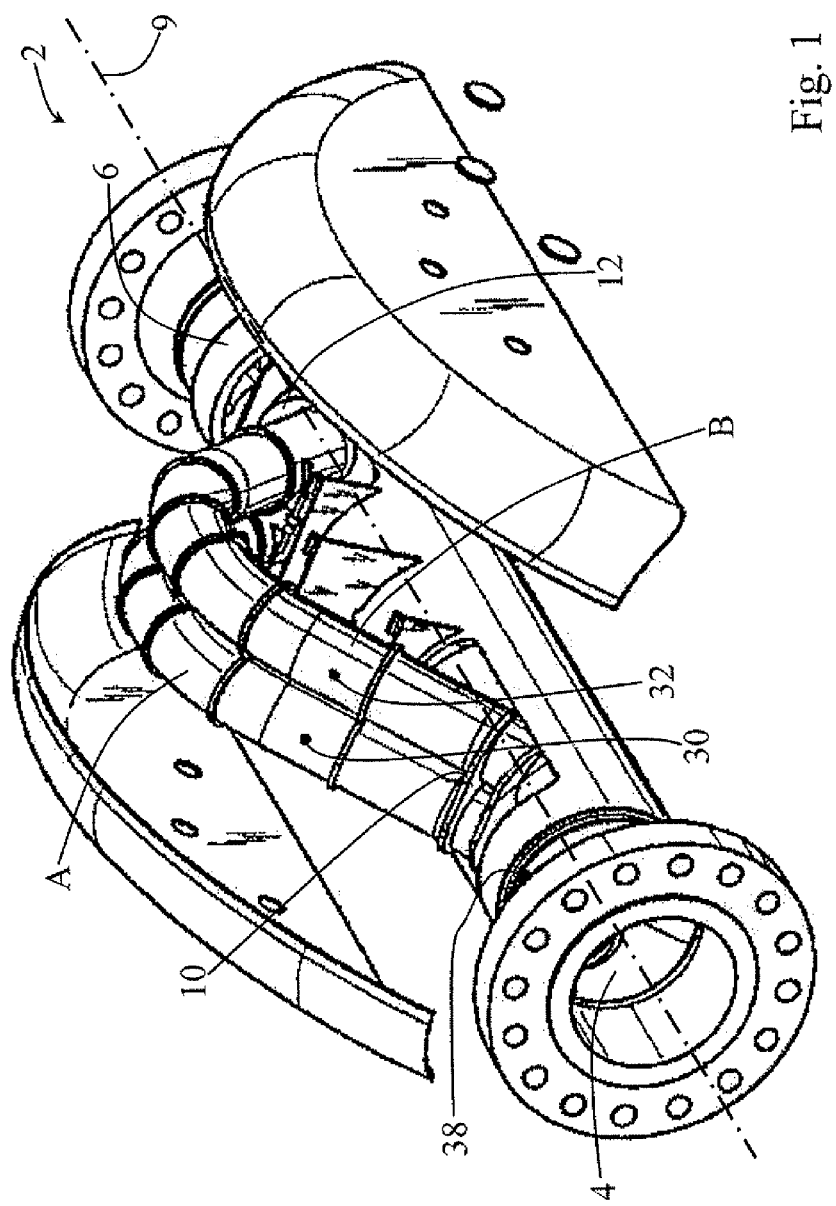
FIG. 1: a schematic representation of a flow measuring device in perspective view, with partially removed housing, for illustrating a form of embodiment of the present invention.
Figure 2:
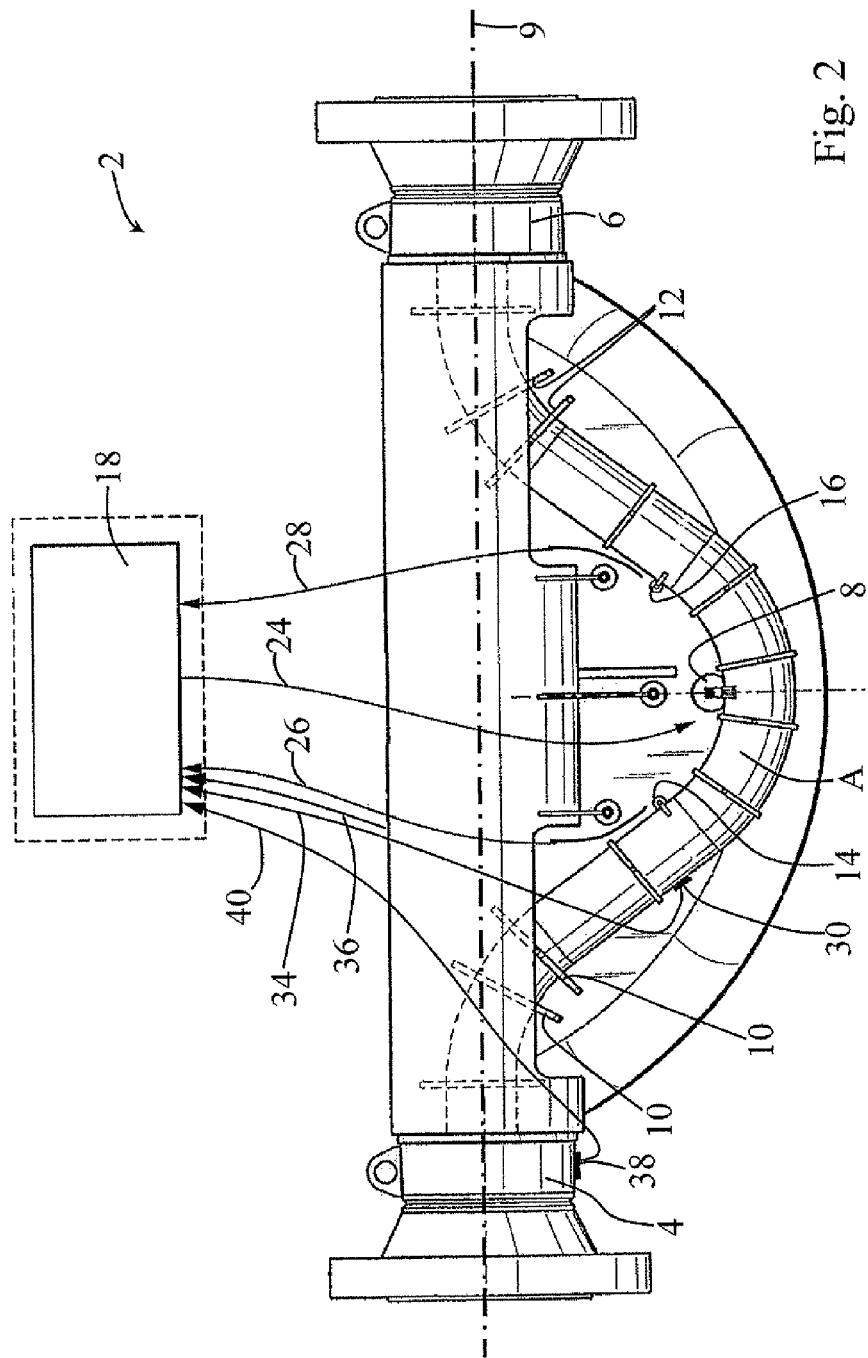
FIG. 2 a side view of the flow measuring device illustrated in FIG. 1, with partially removed housing.

FIGS. 1 and 2 show, by way of example, a flow measuring device 2 embodied for performing the detection method of the invention. Flow measuring device 2 includes two measuring tubes A and B, each of which is curved and extends parallel to the other. Measuring tubes A and B are mounted such that they can oscillate. Flow measuring device 2 is designed to be insertable in a pipeline (not shown). The design of flow measuring device 2 is such that, when it is inserted in a pipeline, medium flowing in the pipeline flows in parallel through the two measuring tubes A and B. To make this happen, the flow measuring device 2 includes on the input side a flow divider 4, by which the medium is divided between the two measuring tubes A and B. On the output side, a flow divider 6 is provided in a corresponding manner, by which the medium emerging from the two measuring tubes A and B is led back together and led to an outlet of the Coriolis flow measuring device 2.

Extending between the two measuring tubes A and B is an exciter 8, which, in the present example of an embodiment, is an electrodynamic exciter. In the case of the present example of an embodiment, exciter 8 is arranged at a maximum/minimum of the curve followed by the two measuring tubes A and B. Exciter 8 is embodied in such a manner that its length is changed by application of an electrical excitation voltage. By applying a corresponding, periodic electrical excitation voltage to exciter 8, the two measuring tubes A and B are periodically pushed apart and/or drawn together, so that they execute bending oscillations. In such case, the two measuring tubes A and B are excited with opposite phase to one another, and in each case execute a swinging movement (with opposite phase to one another) about a longitudinal axis 9 of flow measuring device 2. The two measuring tubes A and B are furthermore mechanically coupled to one another on the input side and on the output side by coupling elements 10, 12.

Extending between the two measuring tubes A and B on their inlet sides and on their outlet sides are two oscillation sensors 14, 16. Mechanical oscillations of the two measuring tubes A and B are registerable via length changes of the two oscillation sensors 14, 16. In the present example of an embodiment, the two oscillation sensors 14, 16 each register change in separation between the two measuring tubes A, B, and, thus, in each case, the combined amplitudes of the two measuring tubes A, B. The oscillation sensors 14, 16 are, for example, electrodynamic oscillation sensors. Evaluation of the sensor signals (or measuring signals) provided by the oscillation sensors 14, 16, and the driving of the exciter 8 are accomplished via a correspondingly embodied electronics 18, which is only schematically presented in FIG. 2 by a box. The driving of exciter 8 via electronics 18 is indicated schematically in FIG. 2 by the arrow 24, while the providing of the sensor signals via oscillation sensors 14, 16 to electronics 18 is presented schematically in FIG. 2 by the arrows 26, 28.

The flow measuring device 2 in the present case is a Coriolis flow measuring device. Accordingly, via the flow measuring device 2, a mass flow of the medium flowing in the respective pipeline is determinable. For this, the two oscillation sensors 14, 16 register, among thing others, a phase shift of the oscillations of the measuring tubes A, B along the direction of elongation of the two measuring tubes A, B. From the registered phase shift, the mass flow can then be ascertained in electronics 18. The flow measuring device 2 is embodied in such a manner that it can also determine density as well as viscosity of the flowing medium.

Depending on medium and process conditions, the measuring tubes A, B are especially endangered as regards accretion and/or abrasion. For performing accretion and/or abrasion detection, temperature sensors 30, 32 are provided on the first measuring tube A and on the second measuring tube B. Temperature sensors 30, 32 are placed on the outsides of the measuring tubes A, B, so that they are thermally coupled via the measuring tube wall of the respective measuring tube A, B to the medium conveyed in the respective measuring tube A, B. During use, the measuring tube walls of measuring tubes A, B are contacted on the inside by the medium. Temperature sensors 30, 32 are the first temperature sensors in the method of the invention. Via temperature sensors 30, 32, a first temperature as a function of time is registerable in each case. In such case, corresponding sensor signals, which are indicated in FIG. 2 by corresponding arrows 34, 36, are provided to electronics 18. Furthermore, a temperature sensor 38 is provided on the outside of the inlet side, flow divider 4 of the flow measuring device 2. It is thermally coupled via the wall of the flow divider 4 to the medium conveyed (during use) within the flow divider 4. Compared to the two first temperature sensors 30, 32 arranged on the measuring tubes A, B, the temperature sensor 38 forms a second temperature sensor of the method of the invention. Via the second temperature sensor 38, a second reference temperature as a function of time is registerable parallel in time to the registering of a first temperature as a function of time via at least one of the two temperature sensors 30, 32. In such case, via the second temperature sensor 38, corresponding sensor signals are provided to electronics 18, this being indicated in FIG. 2 by the arrow 40.

The flow divider 4 has in the region of the second temperature sensor 38 a greater flow cross section and a flow path for the medium extending largely in a straight line. Because of these features, the flow divider 4, at least in this region, is significantly less susceptible to accretion and abrasion than the measuring tubes A, B. The temperature measurement via the second temperature sensor 38 accordingly forms an essentially invariant reference compared to temperature measurement in the region the first temperature sensors 30, 32. In the following, it is assumed that a medium tending toward accretion flows through the flow measuring device 2. In the following, accretion detection of the invention on the first measuring tube A (making use of the first temperature sensor 30 provided on this first measuring tube A) is explained, wherein, in the context of this explanation, reference is additionally made to FIGS. 3A and 3B. The method of the invention, as is readily evident for those skilled in the art, is capable of being put into practice in a corresponding manner also for accretion and/or abrasion detection on the second measuring tube B making use of the temperature sensor 32 provided on this second measuring tube B).

It is assumed that, first of all, a medium with a temperature around room temperature flows through the flow measuring device 2. In the context of a cleaning procedure for the pipelines (CIP: Cleaning In Process), in which the flow measuring device 2 is applied, a medium change is performed, in the case of which hot steam (temperature: 100° C.) flows through the flow measuring device 2. In such case, it can be provided, for example, that the electronics 18 of the flow measuring device 2 is informed of this medium change via a fieldbus communication or that the occurring temperature change of the medium is registered via a temperature sensor (not shown) of the flow measuring device 2 in direct contact with the medium. The temperature adjustment in the region of the first measuring tube A is registered via the first temperature sensor 30. Thus, the latter registers a first temperature as a function of time. Furthermore, as reference, the temperature adjustment in the region of the inlet side, flow divider 4 is registered via the second temperature sensor 38, wherein the latter registers a second reference temperature as a function of time.

Figure 3A:
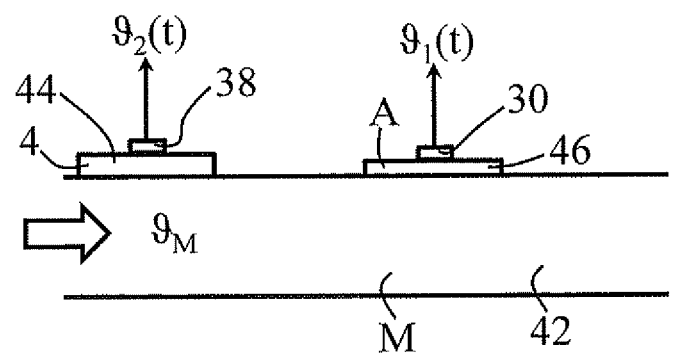
FIG. 3A a schematic representation of the temperature registering via the first and second temperature sensors in a starting state.
Figure 3B:
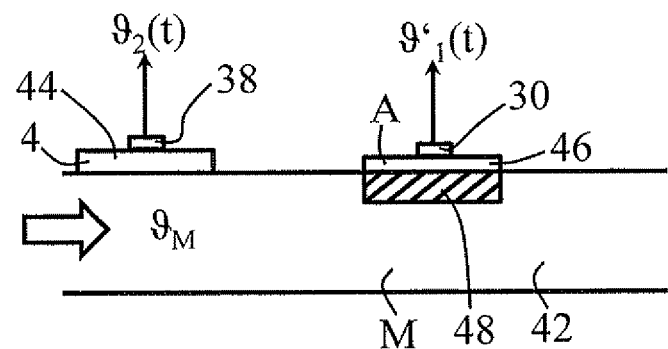
FIG. 3B a schematic representation corresponding to FIG. 3A, with accretion in the region of the first measuring tube.

FIGS. 3A and 3B show, schematically, the influencing factors on the temperature adjustment in the region of the first temperature sensor 30 and in the region of the second temperature sensor 38. In such case, in FIG. 3A, an initial state of the flow measuring device 2 is presented, in which no accretion has occurred within the measuring tubes A, B. In FIG. 3B, in contrast, a state is presented, in which accretion has occurred at least in measuring tube A. In FIGS. 3A and 3B, the flow path 42 of the respective medium M through flow measuring device 2 is presented schematically, wherein only the part extending through the first measuring tube A is shown. The second temperature sensor 38, which is positioned upstream from the first temperature sensor 30, is thermally coupled via the wall 44 of inlet side flow divider 4 to the medium M. As is explained above, this thermal coupling is essentially invariant in time. The first temperature sensor 30, in the case of the initial state illustrated in FIG. 3A, is thermally coupled to medium M exclusively via the measuring tube wall 46 of the first measuring tube A. In the state illustrated in FIG. 3B, in contrast, the thermal coupling of the first temperature sensor 30 occurs additionally via the accretion 48, which is formed on the inside of the measuring tube wall 46. This influences the temperature adjustment in the region of the first temperature sensor 30.

Thus, in the case of the above related situation, if a temperature change of the medium M occurs in such a manner that the medium now has a temperature $\theta_M$ of 100° C., a changed temperature occurs both in the region of the first temperature sensor 30 as well as also in the region of the second temperature sensor 38. In order to register this temperature adjustment, the first temperature sensor 30 registers a first temperature as a function of time, i.e. $\theta_1(t)$ in FIG. 3A and $\theta_1'(t)$ in FIG. 3B, and the second temperature sensor 38 registers, parallel in time thereto, a second reference temperature as a function of time, i.e. $\theta_2(t)$ in FIGS. 3A and 3B. If, in the case of the state in FIG. 3B, the same conditions (apart from the accretion 48 being present) are present as in the case of the initial state in FIG. 3A, then, in the case of both states, the same second reference temperature as a function of time $\theta_2(t)$ is measured via the second temperature sensor 38. In contrast, in the case of the state illustrated in FIG. 3B, the first temperature sensor 30 measures a deviating first reference temperature as a function of time, i.e. $\theta_1'(t)$, than the first temperature as a function of time $\theta_1$ in the case of the initial state. It should here be noted that, for performing the detection method of the invention, it not absolutely required that the same conditions be in each case present as in the case of an earlier performed calibration measurement. In general, a change in the temperature adjustment in the region of the first temperature sensor 30 (or in the region of the first measuring tube A) can be determined by evaluating the first temperature as a function of time and the second reference temperature as a function of time. In such case, different evaluating methods for the first temperature as a function of time and the second reference temperature as a function of time are fundamentally possible, as was explained above. The particular evaluating method to be applied is implemented in the electronics 18 of the flow measuring device 2.

In a variant of an embodiment, which will now be explained with reference to the state in FIG. 3B, the first temperature as a function of time, i.e. $\theta_1'(t)$, is divided by the second reference temperature as a function of time, $\theta_2(t)$. The result of this division is approximated with an approximation function, which, in the present case, is formed by the function $$ae^{-\frac{t}{\tau}},$$

wherein t stands for time, and a, the amplification factor, and τ, the time constant, are parameters of the function and must be fitted to the data. The time constant τ is used as the variable, whose value is characteristic for the heat transfer. This is compared with a predetermined reference variable, which was ascertained earlier in the context of a calibration measurement. If this deviates by more than a limit value from the predetermined reference value, accretion is then detected by the flow measuring device. A signaling of accretion (or, in given cases, abrasion) to a user can, in such case, especially occur via an acoustic and/or visual signal. Additionally or alternatively, it can also be provided that a corresponding report is dispatched by flow measuring device 2 electronically (e.g. via a fieldbus), in order to inform a superordinated unit.

The present invention is not limited to the form of embodiment explained with reference to the figures. Especially, there are various options for positioning the second temperature sensor, via which the second reference temperature as a function of time is measured. For example, the second temperature sensor can also be provided on the second measuring tube B (compare temperature sensor 32 in FIG. 1), and can provide the second reference temperature as a function of time for performing accretion detection on the first measuring tube A. Furthermore, the opportunity exists that the second temperature sensor extends into the flow path of the medium M, and is thus in direct contact with the medium M. Furthermore, still other variables, which especially have an influence on the temperature adjustment in the region of the first and second temperature sensors, can also generally enter into the evaluation for determining the variable characteristic for heat transfer from the medium through the measuring tube wall to the first temperature sensor. Such variables can especially be formed by properties of the medium such as, for example, a flow velocity of the medium, a heat capacity of the medium, an enthalpy of the medium and/or a heat conduction of the medium, etc.

The invention claimed is:

1. A method for detecting accretion or abrasion on a first measuring tube, which is embodied as a first component of a flow measuring device flowed through by medium, said method comprising:
   registering a first temperature as a function of time via a first temperature sensor, which is arranged on the first measuring tube in such a manner that, between the first temperature sensor and the medium, at least one measuring tube wall of the first measuring tube is embodied; and, parallel in time, registering a second reference temperature as a function of time via a second temperature sensor, which is spaced from the first temperature sensor, and is thermally coupled to the medium via at least a second component of the flow measuring device, said second component being provided between the second temperature sensor and the medium and being contacted by the medium;
   determining, from at least the first temperature as a function of time and the second reference temperature as a function of time, at least one variable characteristic for heat transfer from the medium through the measuring tube wall to the first temperature sensor, said at least one variable characteristic for heat transfer being determined from at least one of: the derivative with respect to time of the first temperature as a function of time and of the second reference temperature as a function of time and the derivative with respect to time of a curve obtained via a predetermined, mathematical combining of the first temperature as a function of time and the second reference temperature as a function of time; and
   detecting accretion or abrasion on the first measuring tube, if the at least one determined characteristic variable or a variable derived therefrom deviates by more than a limit value from a predetermined reference variable.

2. The method as claimed in claim 1, wherein:
   the second temperature sensor is arranged in direct contact with the medium.

3. The method as claimed in claim 1, wherein: the second component formed by an inlet side flow divider of the flow measuring device.

4. The method according to claim 1, wherein: the second component is embodied separately from the first measuring tube such that it is essentially invariant as regards accretion and/or abrasion by the medium.

5. The method according to claim 3, wherein:
   the second component is formed by a second measuring tube of the flow measuring device; and
   the second measuring tube is connected so as to be fluidically in parallel with the first measuring tube.

6. The method as claimed in claim 1, further comprising:
   exciting the first measuring tube to execute mechanical oscillations.

7. The method as claimed in claim 1, comprising:
   changing a temperature of the medium.

8. The method as claimed in claim 1, wherein: the flow measuring device is formed by a Coriolis flow measuring device.

9. The method as claimed in claim 1, wherein:
   said step of determining, the first temperature as a function of time and the second reference temperature as a function of time are combined with one another according to a predetermined, mathematical operation, the result obtained therefrom is approximated with a predetermined, mathematical approximation function by conforming corresponding parameters of the approximation function, and the at least one variable characteristic for heat transfer is formed by at least one parameter value of the ascertained approximation function.

10. The method as claimed in claim 9, wherein:
    the predetermined, mathematical operation is a division of the first temperature as a function of time by the second reference temperature as a function of time.

11. The method as claimed in claim 9, wherein:
    the predetermined, mathematical approximation function is formed by the function $$ae^{\frac{t}{\tau}}ae^{\frac{t}{\tau}},$$

wherein a and τ are parameters and t is time.

12. The method as claimed in claim 9, wherein:
    the at least one determined variable characteristic for heat transfer is formed by the parameter value of the time constant of the approximation function.

13. A flow measuring device, via which at least one physical, measured variable of a medium flowing in a pipeline, said measured variable is selected from mass flow, density and/or viscosity of the medium and said flow measuring device comprising:
    a first measuring tube, through which a flow path for at least one part of the respective medium extends;
    at least a first temperature sensor, which is arranged on said first measuring tube in such a manner that, between said first temperature sensor and a flow path extending within said first measuring tube, at least one measuring tube wall of said first measuring tube is present;
    at least a second temperature sensor, which is spaced from said first temperature sensor and is thermally coupled to a section of the flow path extending within the flow measuring device via at least a second component of the flow measuring device, which second component is provided between the second temperature sensor and the medium and being contacted by the medium; and an electronics, wherein:

in that, during use of the flow measuring device, via said electronics, from at least a first temperature as a function of time registered by said first temperature sensor and a second reference temperature as a function of time registered parallel in time by said second temperature sensor, at least one variable, which is characteristic for heat transfer from the respective medium through said measuring tube wall to said first temperature sensor is determinable, and accretion or abrasion on said first measuring tube is detectable, if the at least one determined characteristic variable or a variable derived therefrom deviates by more than a limit value from a predetermined reference variable, and the at least one variable characteristic for heat transfer is determined from at least one of: the derivative with respect to time of the first temperature as a function of time and of the second reference temperature as a function of time and the derivative with respect to time of a curve obtained via a predetermined, mathematical combining of the first temperature as a function of time and the second reference temperature as a function of time.

* * * * *